United States Patent [19]

Sibral et al.

[11] 4,283,548
[45] Aug. 11, 1981

[54] DIISATOIC ACID OR TRIISATOIC ACID DERIVATIVES

[75] Inventors: Walter Sibral, Tulln; Oskar Schmidt, Kittsee, both of Austria

[73] Assignee: Lim-Holding S.A, Luxembourg, Luxembourg

[21] Appl. No.: 28,754

[22] Filed: Apr. 10, 1979

[51] Int. Cl.$^3$ .................. C07D 401/06; C07D 233/64
[52] U.S. Cl. .................................. 548/310; 548/305; 548/312; 544/314; 260/455 R; 560/50; 528/62; 528/64; 528/73
[58] Field of Search .............................. 548/312, 310

[56] References Cited

U.S. PATENT DOCUMENTS

| | | | |
|---|---|---|---|
| 3,755,350 | 8/1973 | Sauli | 548/312 |
| 3,772,326 | 11/1973 | Batzer et al. | 548/312 |
| 3,821,098 | 6/1974 | Garratt et al. | 548/312 |
| 3,864,357 | 2/1975 | Porret et al. | 548/312 |
| 4,122,276 | 10/1978 | Habermeier | 548/310 |
| 4,153,801 | 5/1979 | Schmidt et al. | 548/312 |
| 4,161,594 | 7/1979 | Batzer et al. | 548/312 |

Primary Examiner—Henry R. Jiles
Assistant Examiner—Jane T. Fan
Attorney, Agent, or Firm—Beveridge, DeGrandi & Kline

[57] ABSTRACT

Object of the invention are new diisatoic acid and triisatoic acid derivatives of the general formula I

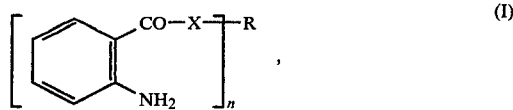

wherein n represents 2 or 3, X stands for oxygen or sulfur and R for a group of the general formula II

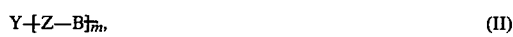

in which m stands for 1 or 2, Y for B when m is 1 and Y further represents a di- or trivalent alkyl group with 1 to 5 carbon atoms when m is 2, B represents alkylene with 1 to 4 carbon atoms and Z stands for phenylene-1,4-dioxy or diphenylene-4,4'-dioxy optionally singly or multiply substituted by Cl, NO$_2$ or alkyl or for a 5- to 7-membered heterocyclic ring which is optionally substituted by one or more of said substituents and has one or more atoms selected from the group consisting of N, S and O as members of the ring, with a benzene nucleus optionally being annulated to said ring, and a process for the production of these compounds which is characterized in that a compound of the general formula III

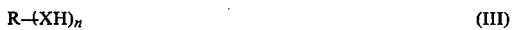

wherein R, X and n have the meaning defined above is reacted with at least two equivalents of isatoic acid anhydride, preferably in the presence of strong bases, as well as the use of these new compounds for the preparation of plastic materials.

9 Claims, No Drawings

DIISATOIC ACID OR TRIISATOIC ACID DERIVATIVES

The invention relates to new diisatoic acid or triisatoic acid derivatives, processes for their production and plastic materials, in particular polyureas and polyurethanes, containing these compounds, and to their production.

It was found that the new di- or triisatoic acid derivatives of the general formula I

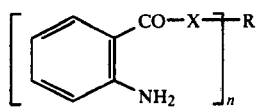

wherein n stands for 2 or 3, X represents oxygen or sulfur and R is a group of the general formula II

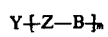

wherein m represents 1 or 2, Y stands for B when m is 1 and Y further represents a di-or trivalent alkyl group having 1 to 5 carbon atoms when m is 2, B represents alkylene having 1 to 4 carbon atoms and Z stands for phenylene-1,4-dioxy or diphenylene-4,4-dioxy optionally singly or multiply substituted by Cl, $NO_2$ or alkyl or stands for a 5- to 7-membered heterocyclic group having one or several N-, S- and/or O-atoms which group is optionally substituted by Cl, $NO_2$ or alkyl and to which optionally a benzene nucleus is annulated, are eminently suitable as chain extenders in the production of polyurethanes and polyureas. They permit a very simple reaction of the reactants, i.e. the starting materials, to the desired plastic materials and endow these with excellent mechanical properties, in particular high structural strength, toughness and thermal stability.

In the production of elastomeric plastic materials of high modulus of elasticity, the structure of the polyadducts has up to now preferably been effected by co-using low-molecular, aromatic diamines, such as 4,4-diamino-3,3-dichloro-diphenyl methane, as chain extenders. In these diamines, the reactivity of the amino groups towards isocyanates is lowered by the chloro atom in ortho- position to the amino group to such an extent that the conditions for the production of plastic materials in the liquid phase are fairly suitable.

The new compounds of the formula (I) according to the invention are less reactive than 4,4-diamino-3,3-dichloro-diphenyl methane. This assures an essentially longer casting time and thus easier processibility, since the time component does not play as important a part as it was and is the case with the chain extenders used up to now. The use of the new compounds of the formula (I) yields plastic materials which are far superior in their properties to those known up to now in respect to thermal stability, tensile strength and structural strength.

In contrast to the diamines used as chain extenders up to now, the new esters according to the invention have moreover no carcinogenic effect.

Preferred are compounds of the general formula I wherein Z stands for a group of the general formula

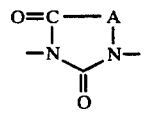

wherein A represents a methylene or ethylene group optionally substituted by up to 4 lower alkyl groups, in particular methyl groups, and the remaining substituents have the meaning indicated above. Particularly preferred are those compounds of the formula I wherein Z represents a group of the formula IV wherein A stands for the group $$\underset{-C-}{\overset{R_1\diagdown\diagup R_2}{\phantom{C}}},$$

wherein $R_1$ and $R_2$ are hydrogen or methyl and the remaining substituents have the meaning defined above.

Further of advantage were found compounds of the general formula I wherein n is 2 or 3, X stands for O or S and R represents a group of the general formula II wherein m is 1 or 2, Y stands for B when m is 1 and for an alkylidene group having 1 to 5 carbon atoms or $$-CH_2\overset{|}{C}HCH_2-$$

when m is 2, B represents an ethylene or isopropylene group and Z is a phenylene dioxy group or a heterocyclic group as defined above.

Particularly preferred, in particular in view of the mechanical properties which they are able to impart to plastic materials, are compounds of the general formula (Ia)

wherein X represents oxygen or sulfur, $R_1$ and $R_2$ independently of one another are lower alkyl, in particular methyl, or hydrogen, B stands for alkylene having up to 4 carbon atoms, in particular the groups $-CH_2-CH_2-$ or $$-\overset{CH_3}{\underset{|}{CH}}-CH_2-$$

and Q is a single bond, a group of the general formula (Ib)

or the general formula

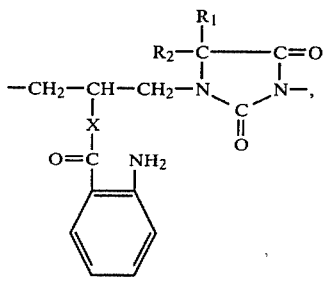

wherein X stands for oxygen or sulfur and $R_1$ and $R_2$ have the meaning indicated above. Further preferred are compounds of the general formula

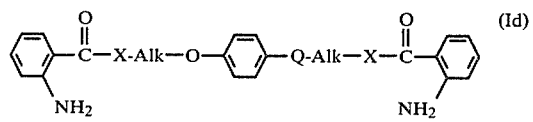

wherein Alk stands for alkylene having up to 4 carbon atoms, in particular for ethylene or isopropylene, X represents oxygen or sulfur and Q is an-O-bridge or a group of the formula

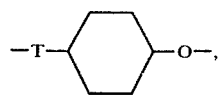

wherein T represents an alkylene group having up to 5 carbon atoms, in particular the group

In addition, the following individual compounds have proven as excellent components for said plastic materials:

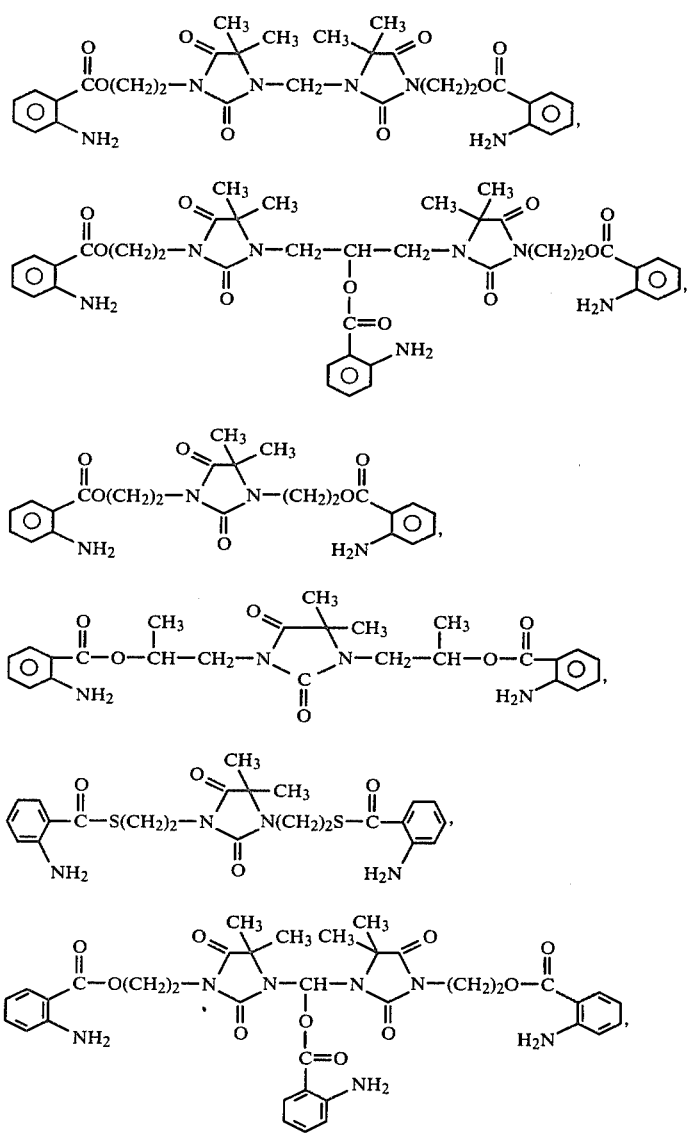

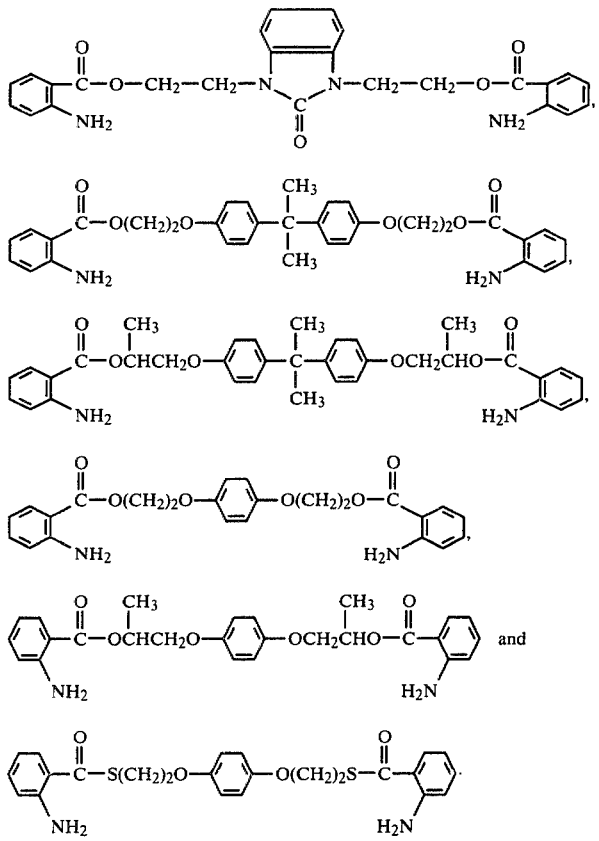

A further object of the invention is a process for the production of the compounds of the above-mentioned general formula I

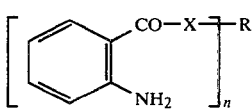  (I)

wherein n stands for 2 or 3, X represents oxygen or sulfur and R is a group of the general formula

  (II)

wherein m represents 1 or 2, Y stands for B when m is 1 and Y further represents a di- or trivalent alkyl group having 1 to 4 carbon atoms and Z stands for phenylene-1,4-dioxy or diphenylene-4,4-dioxy optionally singly or multiply substituted by Cl, NO₂ or alkyl or for a 5- to 7-membered heterocyclic group having one or several N-, S- and/or O-atoms which group is optionally singly or multiply substituted by Cl, NO₂ or alkyl and to which optionally a benzene nucleus is annulated. The process according to the invention is characterized in that a compound of the general formula

  (III)

wherein R, X and n have the meanings defined above is reacted with at least two equivalents of isatoic acid anhydride. The reaction is preferably carried out in the presence of strong bases.

A preferably used starting material of the process is a compound of the general formula III wherein Z stands for a group of the general formula

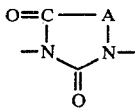  (IV)

wherein A represents a methylene or ethylene group optionally substituted by up to 4 lower alkyl groups, in particular methyl groups, and the remaining substituents have the meaning indicated above.

According to the invention, it is further of advantage to react a compound of the formula III as defined above, wherein Z stands for a group of the general formula IV, wherein A represents the group

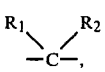

wherein $R_1$ and $R_2$ are hydrogen or methyl and the remaining substituents have the meaning defined above, with isatoic acid anhydride.

It was further found advantageous to produce a compound of the general formula I, wherein n is 2 or 3, X stands for O or S and R represents a group of the general formula II wherein m is 1 or 2, Y stands for B when m is 1 and for an alkylidene group having 1 to 5 carbon atoms or

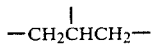

when m is 2, B represents an ethylene or isopropylene group and Z is a phenylene dioxy group or a heterocyclic group as defined above which is characterized in that a compound of the general formula

wherein R, X and n have the meaning defined above are reacted with at least two equivalents of isatoic acid anhydride, preferably in the presence of strong bases.

Due to their favorable properties, it is particularly preferred to produce compounds of the general formula Ia wherein the substituents have the meaning as defined above for compound Ia, by reacting a compound of the general formula

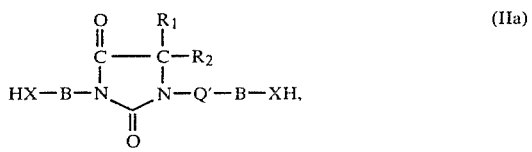

wherein $R_1$, $R_2$, X and B have the meaning defined above and Q' stands for a single bond or for a group of the general formula Ib, as defined above, or by reacting a compound of the general formula

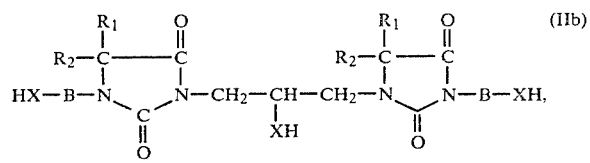

wherein $R_1$, $R_2$, X and B have the meaning defined above, with isatoic acid anhydride. Of the compounds above-mentioned, those wherein $R_1$ and $R_2$ stand for methyl possess favorable properties.

For producing compounds of the formula Id, which also have favorable properties, a (thio) alcohol of the general formula

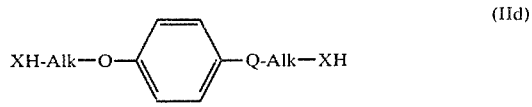

wherein Alk, X and Q have the meaning defined above, is reacted with isatoic acid anhydride.

It is of advantage to carry out the reaction of the compounds of the formula III with at least two or at least three equivalents of isatoic acid anhydride in the presence of strong bases such as NaOH or KOH under heating at temperatures of 30° to 150° C., preferably of 40° to 130° C. The reaction can be carried out in the presence or in the absence of inert organic solvents. The amount of catalyst employed can vary within a wide range, preferably within a range of 1 to 10 parts by weight or base per 100 parts by weight of isatoic acid anhydride employed. The reaction is completed at the termination of gas development. The catalyst and excess isatoic acid anhydride are filtered off, optionally after addition of an inert solvent, the final product is obtained pure either by direct crystallization or by treatment with an acid, shaking with water and subsequent crystallization.

The invention further relates to the use or the application of the above-mentioned compounds of the general formula I or the compounds of the formula I produced as described above for the production of plastic materials or as additives in the production of plastic materials, in particular polyurethanes or polyureas according to the isocyanate polyaddition process. Object of the invention are thus particularly polyureas characterized in that they are produced under use of at least one of the aforementioned compounds of the formula I and a polyisocyanate, and the production of these plastic materials.

The production of the plastic materials under use of the new compounds of the formula I according to the invention or obtainable according to the invention according to the isocyanate polyaddition process can be effected by any given method known in polyurethane chemistry. This means that the reaction of the new compounds with polyisocyanates of all types can be carried out under co-use of all types of additives known in polyurethane chemistry, such as catalysts, flame-retardants and the like.

Suitable polyisocyanates to be employed in the production of the polyadducts under use of the new compounds of the formula I described above are all polyisocyanates known in polyurethane chemistry such as tetramethylene diisocyanate, hexamethylene diisocyanate, 2,4-diisocyanato toluene, 2,6-diisocyanato toluene, mixtures of these isomers, 4,4-diisocyanato diphenyl methane and the like.

Further polyisocyanates preferred according to the invention are solutions of socalled "modified polyisocyanates", i.e. solutions of polyisocyanates having biuret groups in polyisocyanates free of biuret groups and/or solutions of polyisocyanates containing at least two NCO groups and at least one N,N-disubstituted allophanic acid ester grouping in polyisocyanates free of allophanic acid ester groups and/or solutions of reaction products of polyisocyanates and compounds containing di- or polyvalent hydroxyl groups in polyisocyanates free of urethane groups and/or solutions of polyisocyanates containing more than one NCO-group and at least one isocyanuric acid ring in polyisocyanates free of isocyanurate groups.

The solutions of "modified polyisocyanates" preferred according to the invention as a rule contain 1 to 85 percent by weight, preferably 10 to 50 percent by weight, of "modified polyisocyanate".

The production of allophanate polyisocyanates can be effected, for instance, according to German Offenlegungsschrift No. 2 008 064. Preferably used are diisocyanates such as toluylene-2,4-diisocyanate or mixtures thereof with toluylene-2,6-diisocyanate.

Modified polyisocyanates also suitable for use according to the invention are solutions of polyisocyanates having biuret groups in polyisocyanates free of biuret groups.

Preferred according to the invention are solutions of 1 to 85 percent by weight of polyisocyanates having biuret groups, said polyisocyanates having the general formula

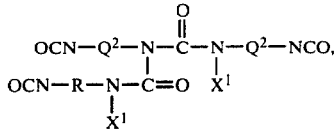

wherein $Q^2$ stands for an alkyl group with 1 to 10 carbon atoms, a cycloalkyl group with 5 to 10 carbon atoms, an aralkyl group with 7 to 12 carbon atoms or an aryl group with 6 to 10 carbon atoms and $X^1$ represents hydrogen or the grouping

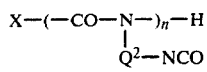

wherein $Q^2$ has the meaning defined above and n is an integer of 0 to 5, in polyisocyanates free of biuret groups, the share of biuret polyisocyanates having more than three isocyanate groups based on the total amount of biuret polyisocyanates amounting to at least 20 percent by weight.

The production of polyisocyanates containing biuret groups can be effected, for instance, according to the teachings of British Patent Specification No. 889 050 or German Patent Specification No. 1 101 394. Polyisocyanates preferred according to the invention are solutions of polyisocyanates containing biuret groups, said polyisocyanates being produced by reaction of 2,4-and/or 2,6-toluylene diisocyanate, 4,4-diphenyl methane diisocyanate and/or its isomers or a mixture of polyisocyanates obtained by aniline formaldehyde condensation and subsequent phosgenation, with water or formic acid, in polyisocyanates free of biuret groups. The polyisocyanates suitable according to the invention preferably contain 0.03 to 5 percent by weight, particularly preferred 0.1 to 2 percent by weight, of chemically bound emulsifiers.

These emulsifiers favorably contain —OH—, amino-, amido-, —COOH—, SH— or urethane groupings and are incorporated into the polyisocyanate by reaction with the isocyanate groups, according, to the teaching of German Offenlegungsschrift No. 1 963 189.

Further suitable isocyanate compounds to be used as starting materials according to the invention are those polyisocyanates containing polyisocyanates having urethane groups and optionally a higher degree of branching then purely difunctional isocyanates. These isocyanates often contain 10 to 70 percent, preferably 20 to 50 percent, of isocyanates having urethane groups, dissolved in polyisocyanates free of urethane groups.

Further suitable modified polyisocyanates are solutions of polyisocyanates hav-ing at least one isocyanuric acid ring in liquid polyisocyanates free of isocyanurate groups. This type of polyisocyanates having isocyanurate groups and processes for their production are described in e.g. German Patent Specification Nos. 951 168, 113 869, 112 285, 1 022 789, 123 729 and British Patent Specification Nos. 89 809, 821 158, 827 120, 856 372, 927 173, 920 080, 952 931, U.S. Pat. Nos. 3,154,522 and 2,801,244, French Patent Specification No. 1 510 342 and Belgian Patent Specification No. 718 994. Preferred polyisocyanates having at least one isocyanuric acid ring are polymeric toluylene-2,4- and/or -2,6-diisocyanates, optionally in mixture with 4,4-diphenyl methane diisocyanate, or its isomers.

The isocyanates to be employed according to the invention are obtained by dissolving the polyisocyanate containing the isocyanurate groups, generally in amounts of 1 to 85 percent by weight based on the weight of the resulting polyisocyanate solutions, in the liquid polyisocyanates free of isocyanurate groups.

Further suitable polyisocyanates free of urethane groups, allophanate groups, isocyanurate groups or biuret groups are aliphatic, cycloaliphatic, aromatic or araliphatic isocyanates such as they are described, for instance, in Liebigs Annalen der Chemie, Vol. 562 (1949), p. 775 ff. Preferred are toluylene dissocyanates or their isomeric mixtures or this type of undistilled isomeric mixtures, diphenyl methane-4,4'-, -2,4'-diisocyanate or undistilled crude material, naphthalene-1,5-diisocyanate, triphenyl methane-4,4'-, 4''-triisocyanate, isophorone diisocyanate, polyphosphonyl polymethylene polyisocyanates obtained by condensation of aniline and/or alkyl substituted anilines with formaldehyde and subsequent phosgenation and isocyanates containing carbodiimide isocyanate adducts, such as they are produced, for instance, according to German Patent Specification No. 1 092 007.

The polyadducts produced under use of the new compounds according to the invention, as already mentioned, have a number of remarkable advantages over polyurethanes of corresponding structure.

EXAMPLE 1

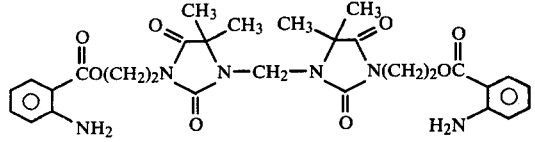

To a solution of 35.6 g methylene-bis-[3-(2-hydroxy ethyl)-5,5-dimethyl hydantoin] in 200 ml dioxan, 1 g of powdered sodium hydroxide and 35.9 g of isatoic acid anhydride are added, the mixture is heated for 4 hours to 80° C. and 1 hour to 100° C., the dioxan is evaporated in vacuo and the residue dissolved in toluene. The insolubles are filtered off, the filtrate is concentrated in vacuo and the residue is crystallized from ethanolwater. This yields 56.4 g (95 percent of the theory) of white crystals with a melting point of 140° C.

Thin layer chromatography on silica gel: Rf (toluene-aceton 3:1)=0.48

IR(KBR): 2.85 and 2.95 ($NH_2$); 3.38 ($C_6H_4$); 5.63 (N—CO—N); 5.85 [N—CO—C ($CH_3$)$_2$—]; 5.95 (ester); 6.18; 6.29; 6.39 ($C_6H_4$); 6.91; 8.05; 13.1; 13.29 and 14.20 μm.

NMR (60mcps, $CDCl_3$):δ = 1.42 (s, 4×$CH_3$), 3.7–4.62 [$A_2B_2$, 2×($CH_2$)$_2$]; 5.02 (s,N—$CH_2$—N); 5.57 (br. s, 2×$NH_2$); 6.40-7.88 (m, 2×$C_6H_4$)ppm.

Analysis: calculated: C: 58.6%; H: 5.72%; N: 14.14%; 0:21.54%. found: C: 58.4%; H: 5.7%; N: 14.0%; 0:21.6%.

EXAMPLE 2

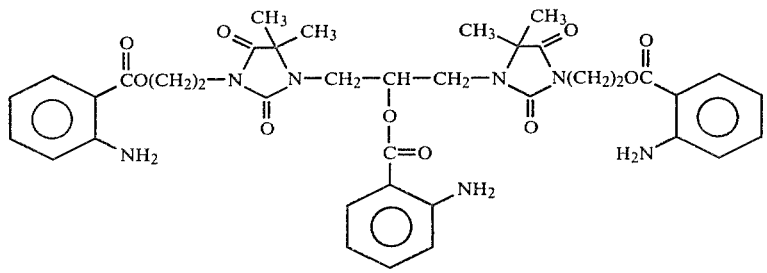

To a solution of 40.04 g of 1,3-di-[3-(2-hydroxy ethyl)-5,5-dimethyl hydantionyl]-2-hydroxy propane in 200 ml dioxan, 1 g of powdered potassium hydroxide and 53.85 g of isatoic acid anhydride are added, the mixture is heated for 7 hours to 80° C. and for 1 hour to 100° C., and subsequently concentrated in vacuo. The residue is dissolved in toluene and the insolubles are filtered off. The filtrate is concentrated in vacuo, the residue applied to a silica gel column and the product is eluated with toluene-acetic acid ethyl ester 7:3. This yields 46.2 g (61 percent of the theory) of the above compound with a melting point of 138° C. Thin layer chromatography on silica gel plates:

Rf (toluene-acetone 3:1)=0.27

EXAMPLE 3

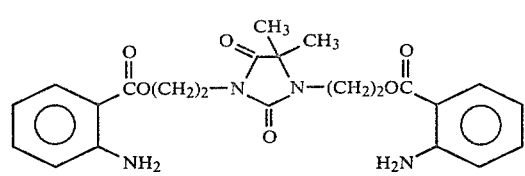

To a solution of 216 g 1,3-di(2-hydroxy ethyl)-5,5-dimethyl hydantoin in 350 ml dioxan, 20 g of powdered potassium hydroxide and 358 g of isatoic acid anhydride are added and the mixture is heated to 100° C. for 4 hours. After cooling, 300 ml toluene are added, the precipitate is filtered off and the filtrate is concentrated in vacuo. The residue is crystallized from ethanol-water. This yields 443.5 g (96 percent of the theory) of white crystals with a melting point of 107° C.

Thin layer chromatography on silica gel plates:
Rf (toluene-acetone 3:1)=0.4
Rf (CHCl$_3$-CH$_3$/H 10:1)=0.52
IR (Nujol): 2.86 and 2.96 (NH$_2$); 5.68 (N—CO—N); 5.89 [N—CO—C—(CH$_{32}$)]; 5.90 (ester); 6.20; 6.30; 6.40 (C$_6$H$_4$); 6.90; 7.75; 8.05; 12.98; 13.30; 14.20 μm.
NMR: (60 mcps, CDCl$_3$): δ=1.37 (s 2×CH$_3$); 3.4–4.13 (m, 2×NCH$_2$); 4.43 (m, 2×OCH$_2$); 5.71 (br. s, 2×NH$_2$); 6.33–8.0 (m, 2×C$_6$H$_4$) ppm.
Analysis: calculated: C: 60.78%; H: 5.76%; N: 12.33%. found: C: 60.97%; H:5.79%; N: 12.20%.

EXAMPLE 4

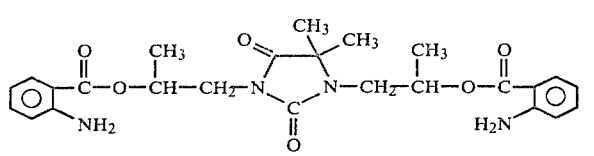

To a solution of 24.4 g 1,3-di(2-hydroxy-2-methylethyl)-5,5-dimethyl hydantoin in 100 ml dioxan, 0.5 g of powdered potassium hydroxide and 48.9 g of isatoic acid anhydride are added, the mixture is heated under agitation first for 6 hours to 90° C. and then for 3 hours to 100° C. The precipitate is filtered off, the filtrate is concentrated in vacuo, the residue is applied to a silica gel column and the product is eluated with toluene-acetic acid ester 8:2. Crystallization from ethanol-water yields 34.2 g (71.2 percent of the theory) of white crystals with a melting point of 115° C.

Thin layer chromatography on silica gel plates: Rf (toluene-acetone 3:1)=0.79

EXAMPLE 5

(a) Preparation of the Starting Compound

Step 1:

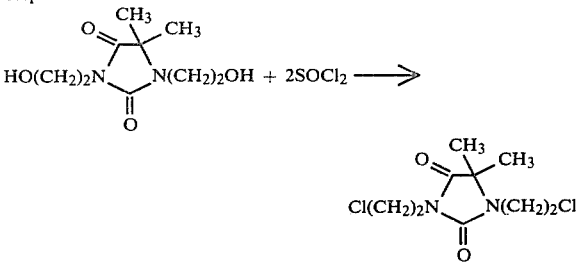

21.6 g (0.1 mol) of 1,3-di-(2-hydroxyethyl)-5,5-dimethyl hydantoin are dissolved in 100 ml toluene, then 29.74 g (0.25 mol) of thionyl chloride are added and the mixture is heated under reflux for 4 hours and then concentrated. The residue is crystallized from ethanol-water. This yields 23.4 g (92.5 percent of the theory) of white crystals with a melting point of 59° C.

Rf(toluene-acetone 3:1)=0.63
NMR: (60 mcps, CDCl$_3$): 1.43 (s, 2×CH$_3$), 3.34–4.0 (2qu., 2×(CH$_2$)$_2$) ppm.
IR: (KBr.): 3.39 (c—H); 5.65 (c=O); 5.85 (c=O); 6.90 (CH$_2$—CH$_3$); 7.55; 7.95; 8.92; 10.50 and 13.10.
Analysis calculated: C: 42.71%; H: 5.58%; N: 11.07%; Cl: 28.01% found: C: 43.03%; H: 5.57%; N: 11.07%; Cl: 27.85%.

(b) Step 2:

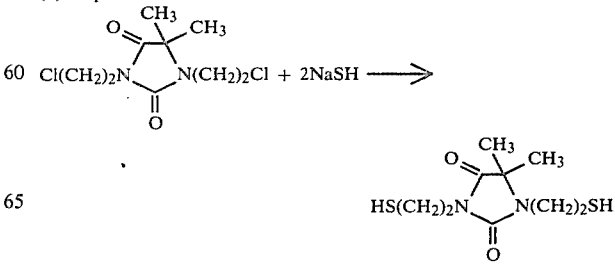

25.3 g (0.1 mol) of 1,3-di-(2-chloroethyl)-5,5-dimethyl hydantoin are dissolved in 100 ml ethanol, then 15 g sodium hydrogen sulfide are added and the mixture is heated under reflux for 5 hours. The reaction mixture is then concentrated, the residue is absorbed in methylene chloride, washed with water three times, dried over sodium sulfate, concentrated and crystallized from methylene chloride-petroleum ether to yield 21.5 g (86.7 percent of the theory).

(c) Preparation of the Compound According to the Invention

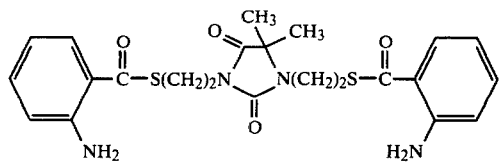

24.8 g. (0.1 mol) of 1,3-di-(mercapto ethyl)-5,5-dimethyl hydantoin are dissolved in 50 ml dioxan, then 2 g of powdered potassium hydroxide and 35.9 g (0.22 mol) of isatoic acid anhydride are added and the mixture is heated under stirring for 8 hours to 90° C. and processed according to Example 1. This yields 46.7 g (96.1 percent of the theory).

EXAMPLE 6

To a solution of 22.2 g of 1,3-di-(2-hydroxyethyl)-benz-imidazol-2-on in 500 ml dioxan, 0.5 g of powdered potassium hydroxide and 48.9 g of isatoic acid anhydride are added and the mixture is heated under stirring for 2 hours to 70° C. The precipitate is then filtered off and washed with methylene chloride. This yields 40.9 g (89 percent of the theory) of white crystals melting at 215° C.

Thin layer chromatography on silica gel plates:
Rf (toluene-acetone 3:1)=0.39

EXAMPLE 7

63.2 g of 2,2-di-[4-(2-hydroxy ethoxy)-phenyl]-propane are melted, then 71.8 g of isatoic acid anhydride and 3 g of powdered sodium hydroxide are added and this mixture is heated for 4 hours to 110° C. 50 ml toluene are then added to the reaction mixture, the insolubles are filtered off and the filtrate is slowly stirred under addition of 100 ml petroleum ether. The precipitate thus formed is filtered off and crystalized from acetone-ethanol-water to obtain white crystals melting at 125° C.

Thin layer chromatography on silica gel plates:
Rf (toluene-acetone 3:1)=0.51

IR (KBr): 2.85 and 2.95 ($NH_2$); 3.38 ($C_6H_4$); 5.92 (ester); 6.2; 6.3; 6.63; 6.72; 6.90; 7.77; 8.42 and 12.0 μm.

NMR: (60 mcps, $CDCl_3$):δ=1.67 (s, 2×$CH_3$); 4.07–4.82 [m, 2×$(CH_2)_2$]; 5.55 (br.s, 2×$NH_2$); 6.35–8.0 (m, 4×$C_6H_4$) ppm.

Analysis: calculated: C: 71.46%; H: 6.18%; N: 5.05%; O: 17.31%. found: C: 71.5%; H: 6.2%; N: 5.3%; O: 17.2%.

EXAMPLE 8

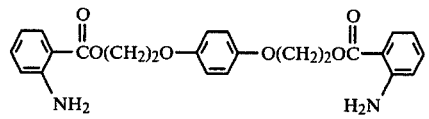

67 g (0.5 mol) of 1,4-di-(2-hydroxyethoxy)-benzene are suspended in 300 ml dioxan, then 5 g of powdered potassium hydroxide and 179.5 g (1.1 mol) of isatoic acid anhydride are added and the mixture is heated under stirring for 10 hours to 90° C. The reaction mixture is then concentrated, the residue is treated with 300 ml methylene chloride and the insolubles are filtered off. The filtrate is washed three times at pH 9 and twice at pH 7, dried over sodium sulfate and concentrated. The residue is crystallized from benzene to obtain pale yellow crystals melting at 125° C.

EXAMPLE 9

(a) Preparation of the Starting Compound

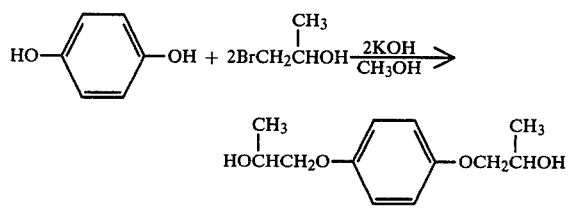

To a solution of 11.1 g (0.1 mol) of hydroquinone in 100 ml of methanol, 11.2 g (0.2 mol) of powdered potassium chloride are added, followed by 30 minutes stirring at room temperature and addition of a solution of 41.7 g (0.3 mol) 1-bromo-2-propanol in 100 ml methanol. This mixture is left standing at room temperature for two hours and then heated under reflux for two hours. The solution is concentrated, the residue is washed with water three times at pH 9 and twice at pH 7, dried over sodium sulfate and concentrated in vacuo. The residue is crystallized from ethanol-water to obtain 16.95 g (75 percent of the theory) of white crystals.

(b) Preparation of the Desired Compound

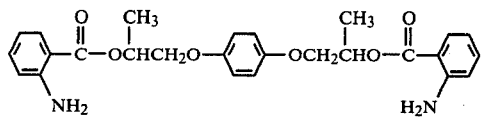

To a solution of 22.6 g (0.1 mol) of 1,4-di-(2-hydroxypropyloxy)-benzene in 50 ml dioxan, 2 g of powdered potassium hydroxide and 35.9 g (0.22 mol) of isatoic acid anhydride are added and the mixture is heated for 10 hours to 90° C. Further processing according to Example 8 yields 41.3 g (89 percent of the theory) of white crystals.

EXAMPLE 10

(a) Preparation of the Starting Compound

Step 1:

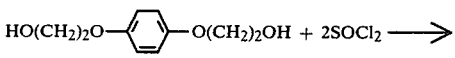

-continued

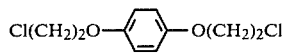

19.8 g (0.1 mol) of 1,4-di-(2-hydroxyethoxy)-benzene are dissolved in 100 ml toluene, then 35.67 g (0.3 mol) of thionyl chloride are added, the mixture is heated under reflux for 4 hours, concentrated and finally crystallized from ethanol-water to obtain 21.3 g (90.7 percent of the theory).

(b) Step 2:

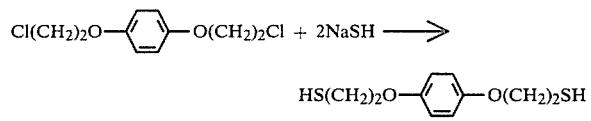

23.49 g (0.1 mol) of 1,4-di-(2-chloroethoxy)-benzene are dissolved in 100 ml ethanol, followed by the addition of 16.8 g (0.3 mol) of sodium hydrogen sulfide and heating under reflux for 5 hours. The reaction mixture is concentrated, the residue is dissolved in methylene chloride, washed with water three times, dried over sodium sulfate, concentrated and crystallized from methylene chloride-petroleum ether to obtain 19.8 g (86.1 percent of the theory) of white crystals.

(c) Preparation of the Compound According to the Invention

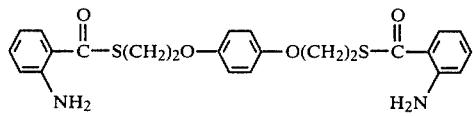

23.0 g (0.1 mol) of 1,4-di-(2-mercaptoethoxy)-benzene are dissolved in 50 ml dioxan, followed by the addition of 1 g powdered potassium hydroxide and 35.9 g (0.22 mol) of isatoic acid anhydride and heating under reflux to 90° C. for 8 hours. Further processing according to Example 8 yields 44.7 g (95.5 percent of the theory).

The new compounds are eminently suitable as chain extenders in the preparation of polyurethanes and polyureas. They permit a very simple reaction of the starting materials to the desired plastic materials and endow these with excellent mechanical properties, in particular with high structural strength, toughness and thermal stability.

What is claimed is:

1. A compound of the formula I

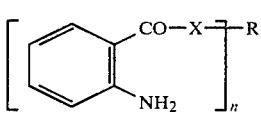

wherein n represents 2 or 3, X stands for oxygen or sulfur and R for a group of the formula II

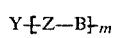 (II)

in which m stands for 1 or 2, Y for B when m is 1 and Y further represents a di- or trivalent alkyl group having 1 to 5 carbon atoms when m is 2, B represents alkylene having 1 to 4 carbon atoms and Z is

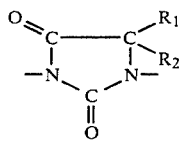

wherein $R_1$ and $R_2$ independently of one another are hydrogen or methyl.

2. A compound of the formula

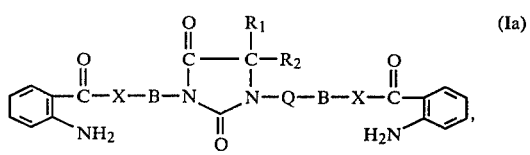 (Ia)

wherein X represents oxygen or sulfur, $R_1$ and $R_2$ independently of one another are lower alkyl or hydrogen, B stands for alkylene having up to four carbon atoms and Q is a single bond or a group of the formula

 (Ib)

or of the formula

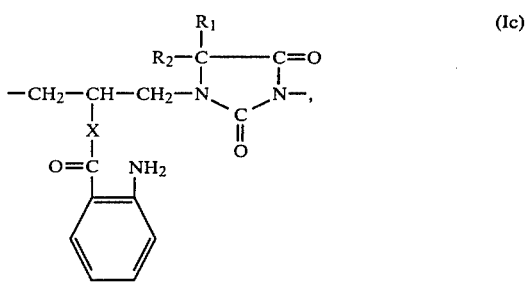 (Ic)

in which formula X stands for oxygen or sulfur and $R_1$ and $R_2$ have the meaning indicated above.

3. A compound of the formula Ia according to claim 2, wherein B stands for the group —CH$_2$—CH$_2$— or

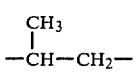

and the remaining symbols have the meaning indicated in claim 2.

4. A compound of the formula

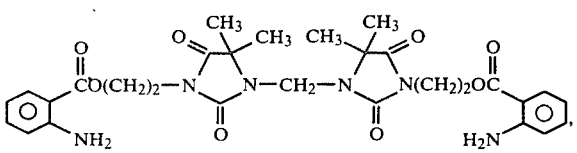

5. A compound of the formula

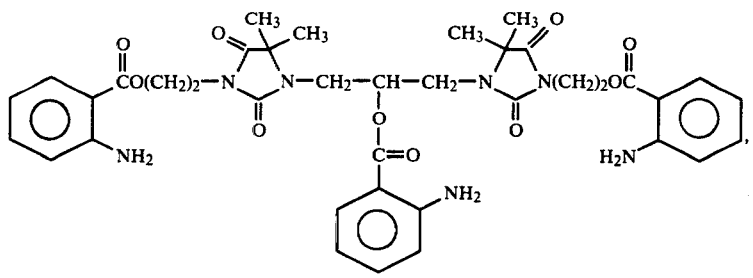
6. A compound of the formula
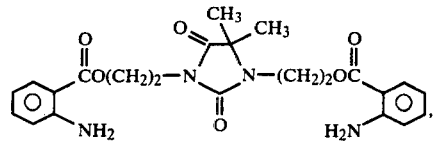
7. A compound of the formula
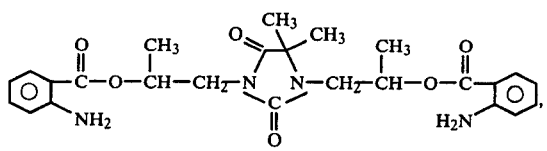
8. A compound of the formula
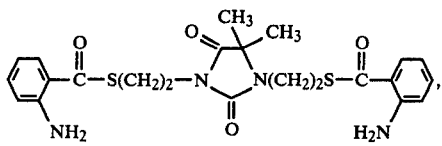
9. A compound of the formula
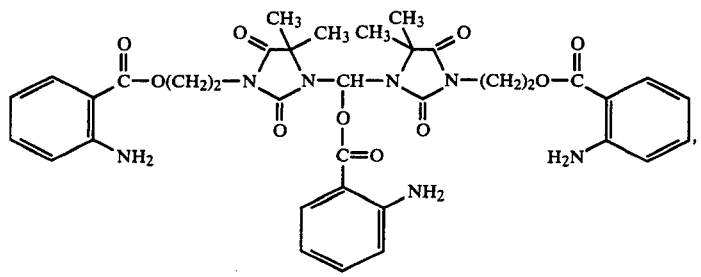
* * * * *